United States Patent
Wilkinson et al.

(10) Patent No.: US 6,239,190 B1
(45) Date of Patent: May 29, 2001

(54) ENHANCEMENT OF ACTIVATION FOR 'BIOLOGICAL' TISSUE ADHESIVES, BONDING AGENTS AND SEALANTS USING "COLOR CHANGE" CHROMOPHORES

(75) Inventors: Francis Wilkinson, Loughborough; David John Mandley, Sheffield, both of (GB)

(73) Assignee: Tissuemed Limited, West Yorkshire (GB)

( * ) Notice: Subject to any disclaimer, the term of this patent is extended or adjusted under 35 U.S.C. 154(b) by 0 days.

(21) Appl. No.: 08/900,761

(22) Filed: Jul. 28, 1997

Related U.S. Application Data

(63) Continuation of application No. PCT/GB96/00181, filed on Jan. 29, 1996.

(30) Foreign Application Priority Data

Jan. 27, 1995 (GB) .................................................. 9501579

(51) Int. Cl.⁷ .................................. C08F 2/46; C08F 2/50
(52) U.S. Cl. ..................................... 522/87; 522/2; 522/9; 522/26; 522/63; 522/72; 522/75; 522/913; 156/336; 156/328; 156/275.5; 156/275.1; 156/275.3; 156/272.2

(58) Field of Search .................................. 522/75, 74, 78, 522/76, 77, 79, 80, 2, 9, 26, 63, 62, 72, 87, 913; 156/272.2, 275.1, 275.3, 275.5, 328, 336

(56) References Cited

U.S. PATENT DOCUMENTS

| 5,209,776 | * | 5/1993 | Bass et al. ........................ 106/124.1 |
| 5,292,362 | * | 3/1994 | Bass et al. ...................... 106/173.01 |
| 5,631,019 | * | 5/1997 | Marx .................................... 424/450 |
| 5,651,982 | * | 7/1997 | Marx .................................... 424/450 |
| 5,665,063 | * | 9/1997 | Roth et al. ............................. 604/53 |
| 5,741,323 | * | 4/1998 | Pathak et al. ........................... 623/1 |
| 5,779,673 | * | 7/1998 | Roth et al. ........................... 604/101 |
| 5,849,035 | * | 12/1998 | Pathak et al. ........................... 623/1 |
| 5,989,244 | * | 11/1999 | Gregory et al. ........................ 606/8 |

* cited by examiner

*Primary Examiner*—James J. Seidleck
*Assistant Examiner*—Sanza L. McClendon
(74) *Attorney, Agent, or Firm*—Frost Brown Todd LLC

(57) ABSTRACT

There is disclosed a method for effecting a reaction by irradiating a substance which absorbs the radiant energy until the reaction is complete and the absorbency of the material changes so as to reduce or cease absorption of further radiant energy.

11 Claims, No Drawings

ENHANCEMENT OF ACTIVATION FOR 'BIOLOGICAL' TISSUE ADHESIVES, BONDING AGENTS AND SEALANTS USING "COLOR CHANGE" CHROMOPHORES

This application is a continuation of Great Britain Patent Application No. 9501579.8 (filed Jan. 27, 1995) and PCT Application No. PCT/GB96/00181 (filed Jan. 29, 1996).

This invention relates to particularly but not exclusively, the effective "setting" or "curing" of an adhesive and more particularly still to effecting the setting of a tissue bonding adhesive or sealant.

WP 92/02238 discloses compositions of various predominantly 'biological' adhesives to bond separated tissues together or to coat tissues or prosthetic material, to enhance strength and water-tightness upon the application of energy and particularly compositions activated by radiation not least laser radiation. Thus a stronger bio-compatible bond or coating is formed. The formation of such a bond or coating being referred to generally hereinafter as "setting" the adhesive.

Such adhesives may be used instead of suturing and stapling for example in surgical procedures for repair or the creation of anastomoses.

The application of a suitable biocompatible adhesive offers many advantages to patient and surgeon alike. It avoids penetration of tissues by needles, as well as immediately sealing the treated tissue. It would prevent or minimize foreign body reaction and scarring. Such a suitable substance could be quicker to apply and may well be more accurate than standard suturing—particularly where small vessels or sutures are concerned. There is also the potential advantage, that if the "setting" energy is sufficiently low, analgesic may not be required. There are many different applications for such a material, not only for bonding anastomoses but also for dressings, hemostats and sealants.

The 'ideal' adhesive would be non-toxic and biocompatible, strong and supple. It would not unduly swell after setting, would be user-friendly to apply and would be easy to sterilize and prepare.

WO 92/02238 refers to prior art fibrin adhesives as well as other multicomponent adhesives. It suggests essentially a two main component adhesive comprising natural or synthetic peptides. These proteins/peptides may be modified ansymetically, chemically or otherwise. They may thus be shortened/cleaved, cross-linked, oxidized or hydrolysed, as a whole or be derivatives of subunits thereof. The original protein with or without modification may be added to by fibrous or structural proteins—for example synthetic or natural collagen, elastin keratin, fibrin, fibronactin and others. Examples of serum proteins, albumin, various globulins and others are given. All these proteins or their derivatives or additives act as the first component constituents.

The second component is said to be generally selected from constituents supporting the first component, such as forming a matrix, gel or sol therewith, usually natural or synthetic proteoglycens, glycoproteins, saccharides, gelatins or polyalcohols and others. Again these components may be modified. Micropolysaccharides, typically glysoaminoglycans including hyaluroric acid its salts, chondroitin sulphate, heparan sulphate may be incorporated.

Other additives may be used, examples being polyvalent cations eg. calcium. These may act as bonding enhancers. Additional components such as pH modifiers, citric acid, ascorbic acid may be used together with preservatives, surfactants and EDTA. The composition of these ingredients and others may be modified in concentration and variations in the molecular weight of constituents also altered to suit the application and the purpose. Viscosity may be changed from liquid to a viscous gel. Additions of non-Newtonian fluids may offer altered physical properties such as pseudoplasticity which may change a relatively viscous material to a liquid under shear forces eg. by syringe injection.

In some circumstances the combination of peptides and other previously mentioned constituents may spontaneously set, thus for example uniting arterial edges to form a 'weld'. In other cases it is necessary to activate the composition with energy and/or photons. Whilst a variety of energy/photon sources have been proposed, most preferable are lasers, including those in the visible or IR ranges, a number of such are mentioned including Nd:YAG and Argon Lasers. UV sources may also be used. A major advantage of lasers is the precise application of laser energy to selected areas, made possible by the coherent nature and hence narrow beam feature of laser emission. Importantly the beam can be very easily and conveniently directed even to difficult access surgical sites by using optical fibre arrangements.

The use of endogenous or exogenous chromophores significantly enhance laser use. Incorporating suitable chromophores into the adhesive has several advantages. The chromophores, of which many have been quoted and used, selectively absorb the laser light energy and convert that energy to thermal energy where it has been applied. The chromophore is chosen for any specific wavelength. The heat generated then sets the adhesive. Thus chromophores enhance accuracy and distribute setting energy. Suitably chosen chromophores will also help reach setting temperatures quickly, thus reducing the time factor for laser application and importantly the overall energy requirements. On account of the selectivity of the chromophores for any given wavelength and the accuracy of such a system, thermal injury to tissue is significantly reduced or avoided.

The benefits of the combination of chromophores and laser may be further enhanced by partially setting the adhesive before ultimate application. This further reduces the final setting energy levels and has obvious clinical advantages.

There are a few major potential problems using lasers for bonding or motivating adhesives or indeed using other energy sources. The time taken for setting or bonding is usually a few seconds. Exposure of just a few more seconds may damage the underlying tissue being treated or other surrounding tissue. The operator will usually see a faint glow when the appropriate setting temperature has been obtained. However this is unreliable and indeed may be difficult in taxing surgical application or conditions. It is thus relatively easy for the operator to either under-irradiate or over-irradiate.

This invention describes the use of "colour change" chromophores which will demonstrate to the operator that the suitable end point has been reached. More importantly, the invention gives further protection and confidence to the operator by comprising of a method, effecting such a reaction by irradiating a substance which absorbs the radiant energy until the reaction is sufficiently complete and the absorbence of the material changes so as to significantly reduce or cease absorption of further energy. Thus not only has the end point been clarified, but also safety as been enhanced by reducing the possibility of further potentially damaging energy being absorbed.

The reaction may comprise the setting of an adhesive such as a composition which bonds to living or other tissue or other materials. In the living tissue situation the components may be modified to enhance structural heating and to encourage cellular ingrowth.

The substance with or without additional components may comprise of a chromophore or group of chromophores which changes per se following irradiation or which reacts with another substance eg. ascorbic acid, to change in the conditions brought about by irradiation.

The method may be used to effect setting of an adhesive or potential adhesive applied to living or other tissue, in which the adhesive is irradiated with radiation which is poorly absorbed by the tissue but well absorbed by the adhesive until it changes colour, which prevents undesirable effects as a consequence of over-irradiation.

The substance may be irradiated by laser light to effect the reaction, which may be in the IR, visible or UV region of the spectrum. The choice of wavelength and chromophore may be altered for different applications.

The Argon laser at 488 and 514 nm is suitable for many applications. Laser power output may be altered, 0.15 W–0.3 W being commonly used. Power may be reduced to 0.05 W in thermally pre-treated adhesives, eg. pre-treatment in which the material is incubated to approximately 70% of setting temperature for 1–2 hours.

Irradiation times of some 10 seconds are commonly applied at 0.2 W for small diameter anastomoses using the Argon laser, but may be varied. Preferably the chromophore's absorption should reduce to a level at which the same laser power could be applied as long again or twice as long again without giving rise to further thermal damage.

Laser spot sizes may also be altered for different application. Frequently a spot size of 1 nm diameter has been used. Power density may also be varied. Commonly 10 $W/cm^9$ is used.

This invention also comprises an additive for a tissue adhesive adapted to absorb radiation to set the adhesive and when the adhesive is set, to change so as to reduce or cease absorption of radiation. The additive may comprise a radiation absorbing substance convertible on irradiation to give a reduced absorption or non-absorbing substance.

Thus the additive may comprise a chromophore and a reactant therefore adapted to effect the conversion—for example a suitable red/orange coloured dye having an absorption maximum in the 400–520 nm region for use with an Argon laser.

Several examples of such a dye are available, such as fuchsin, phloxin, erythrosin and eosin. They may be presented dissolved in say Ringers Solution and may have a concentration between 0.1 $mol/dm^3$ and 0.05 $mol/dm^3$ but may be varied. Other solutions may be used as illustrated in later examples.

The additive may comprise a reducing agent as a conversion effecting reagent. The reducing agent may comprise for example, ascorbic acid which may be present at 0.11 $mol/dm^3$ concentration or EDTA which may be present at 0.2 $mol/dm^3$ concentration.

The invention also comprises a tissue bonding adhesive containing the additives or similar appropriate additives described above. The adhesive may comprise albumin, which may be in solution, eg. in Ringers solution between 10 and 40% w/w or other appropriate solutions.

Adhesives containing additives and modifications according to the invention may be used in a variety of circumstances and be presented, applied and prepared in many ways. In addition to vascular anastomoses, gut, ureteric and urethral applications may be used. Tissues of all descriptions, including liver and kidney may be repaired both by application to lacerated areas as well as by closing hemorrhagic sites. They may also be applied directly or endoscopically to areas of resected or damaged lung parenchyma. They may also be applied to seal drainage tubes or to seal areas after tube removal.

The various adhesive recipes may be coated and/or pre-treated (as required) onto patches of material, synthetic or biological or onto prostheses, such as vascular prostheses, to aid joining such prostheses to the free ends or sides of veins or arteries—for example in bypass procedures. They may also be used for sealing or coating vascular grafts.

The invention is not limited to the additives, dyes, solvents, adhesives and reagents disclosed above, nor to the use of the same for the purpose referred to. Nevertheless, it is anticipated, that a very important application of the method and the additives and adhesives will be in the area of human and veterinary surgery and that a range of adhesives and additives suitable therefore will be developed for different purposes and applications in that area.

EXAMPLES OF ADHESIVES CONSTITUENTS SUPPORTING THE INVENTION

These examples demonstrate the potential benefits of a colour change chromophore which fades of changes colour and therefore alters absorption following the setting process.

Example 1

Non-fading Chromophore Solution (Bovine albumin, heparan sulfate, chrondroitin sulphate A and eosin Y)

1. Bovine Albumin 0.4 g of lyophilized powder Bovine albumin (Sigma Chemicals A2153) dissolved in 1 $cm^3$ of Ringers solution. (Small amounts of powdered bovine albumin added gradually to the stirred Ringers solution)

2. Chondroitin Sulphate 0.1 g of chondroitin sulphate A (sodium salt) (Sigma Chemicals C 9819) dissolved in 1 $cm^3$ of Ringers solution. Same method to dissolve as bovine albumin.

3. Heparan Sulphate

To the 1 $cm^3$ solution of bovine albumin prepared in stage 1, added 0.28 mg of heparan sulphate (sodium salt) (Fluke biochemicals 51541). Stirred solution slowly to ensure heparan sulphate had dissolved.

4. Eosin Y. Chromophore

To the 1 $cm^3$ solution of bovine albumin/heparan sulphate prepared in stages 1 and 3, added a visible light absorbing chromophore EOSIN Y. (Aldrich Chemicals 31,983-0).

Consisted of 0.01359 g of Eosin Y in 1 $cm^3$ bovine albumin/heparan sulphate mixture.

Concentration of Eosin Y:

$$\frac{\frac{0.01359 \times 1000}{691.86}}{1} = 0.0196 \, mol/dm^3$$

SPLIT THE 1 $cm^3$ SOLUTION OF BOVINE ALBUMIN/HEPARAN SULPHATE/EOSIN INTO TWO 0.5 $cm^3$ FRACTIONS.

T. one 0.5 $cm^3$ fraction added 0.2 $cm^3$ of the chondroitin sulphate A solution prepared in stage 2.

Example 2

Fading Chromophore Solution
(Bovine Albumin, heparan sulphate, chondroitin sulphate A, eosin Y and EDTA).

1. To the second 0.5 cm$^3$ fraction of bovine albumin/heparan sulphate/eosin Y prepared for example 1, added 0.2 cm$^3$ of the Chondroitin Sulphate A solution (stage 2 EXAMPLE 1)

PLUS

2. Ethylenediaminetetraacetic acid (EDTA) (The chemical responsible for dye fading)

Prepared a solution of EDTA (disodium salt dihydrate) (Aldrich Chemicals 25,235-2) consisting of 0.77298 g of EDTA in 10 cm$^3$ Ringers solution.

Concentration of EDTA $$\frac{\frac{0.77298 \times 1000}{372.24}}{10} = 0.20 \text{ mol/dm}^3$$

ADDED TO 0.1 cm$^3$ OF THE 0.20 mol/dm$^3$ SOLUTION PREPARED ABOVE (STAGE 2) TO 0.7 cm$^3$ OF THE BOVINE ALBUMIN CHONDROITIN SULPHATE A SOLUTION.

When combined with bovine albumin/heparan sulphate/eosin y/chondroitin sulphate, the concentration of EDTA is 0.025 mol/dm$^3$.

Burst Pressure Results Using These Solutions

End to end anastomoses of porcine splenic arteries, prepared using a laser power of 0.2 watts and spot size of 1 mm.

Example 1

No Dye Fading 138.1, 250, 446.5, 219.8, 421.6, 272.7, 85.4, 89.7 mm/Hg

Example 2

With Dye Fading 495.8, 259.2, 302.6, 482.4, 403.9, 366.9, 317.6, 296.3, 291.2 mm/Hg. Eosin Chromopshore+Bovine albumin+Heparan sulphate+Chondroitin sulphate with and without EDTA (fading agent). BURST PRESSURES (mmHG) 0.2 W

| Condition | With EDTA (9) | Without EDTA(8) |
|---|---|---|
| Mean | 358.06 | 240.5 |
| Standard deviation | 80.7 | 129.5 |
| 95% confidence limit | 292.2–420.1 | 132.2–348.8 |

COMMENT: Although these were not appreciable time differences for performing the anastomoses in either group, the bursting pressures were significantly higher in the chromophore fading group. Histological examination of both groups demonstrated significant thermal injury in the group without fading chromophores and no injury or minimal thermal damage in the chromophore fading group.

This invention of a colour change chromophore, giving a clear "endpoint" for laser radiation used for setting adhesives, enhances the performance and safety of such adhesives.

What is claimed is:

1. A method for effecting a setting of an adhesive composition which bonds to animal tissue, wherein the adhesive composition contains a substance which absorbs radiant energy until the setting of the adhesive composition is complete and which also changes absorbency upon the setting of the adhesive composition so as to reduce or cease absorption of further radiant energy, wherein the method comprises applying the adhesive composition to animal tissue and irradiating the adhesive composition with radiant energy until the absorbency of the adhesive composition changes.

2. A method according to claim 1, wherein the adhesive composition contains a chromophore which changes upon irradiation or which reacts with another substance upon irradiation to change the chromophore of the adhesive composition.

3. A method according to claim 2, used to effect the setting of the adhesive composition applied to animal tissue, wherein the adhesive composition is irradiated with radiation which is poorly absorbed by the tissue but is well absorbed by the adhesive composition until the absorbency of the adhesive composition changes.

4. A method according to claim 3, wherein the adhesive composition is irradiated with laser light to effect the setting.

5. A method according to claim 4, wherein the laser light is in the visible spectrum.

6. A method according to claim 4, wherein the laser light is in the infrared spectrum.

7. A composition comprising a biological tissue adhesive and an additive, wherein the tissue adhesive is adapted to absorb radiation which upon absorption of radiation promotes a setting of the tissue adhesive, characterized by the additive substantially or completely ceasing to absorb radiation when the adhesive is substantially set.

8. The composition of claim 7 wherein the additive comprises a radiation absorbing chromophore which changes upon irradiation or which reacts with a conversion effecting reagent upon irradiation to change the chromophore of the additive.

9. The composition of claim 8 wherein the additive is a dye with an absorption maximum in the 400 nm to 520 nm region of the electromagnetic spectrum.

10. The composition of claim 9 which also comprises a reducing agent as the conversion effecting reagent.

11. The composition of claim 10 wherein the adhesive comprises albumin.

* * * * *